United States Patent [19]

Bergman

[11] 4,141,689
[45] Feb. 27, 1979

[54] METHODS AND DEVICES FOR DETERMINING THE CONCENTRATION OF A COMPONENT OF A FLUID

[75] Inventor: Imanuel Bergman, Sheffield, England

[73] Assignee: National Research Development Corporation, London, England

[21] Appl. No.: 760,709

[22] Filed: Jan. 19, 1977

[30] Foreign Application Priority Data

Jan. 21, 1976 [GB] United Kingdom ............... 02338/76

[51] Int. Cl.² ..................... G01N 31/00; G01N 31/06; G01N 31/08
[52] U.S. Cl. ............................... 23/232 R; 23/230 R; 23/232 C; 23/232 E; 422/89; 422/93; 422/98
[58] Field of Search ............. 23/232 R, 232 E, 254 R, 23/254 E, 255 R, 255 E, 232 C

[56] References Cited

U.S. PATENT DOCUMENTS

| | | | |
|---|---|---|---|
| 2,149,441 | 3/1939 | Jacobson | 23/232 E |
| 2,899,282 | 8/1959 | Eyraud | 23/255 E |
| 2,980,513 | 4/1961 | Kapff | 23/255 E |
| 3,590,628 | 7/1971 | Orr | 23/254 E X |
| 3,753,653 | 8/1973 | Brieva et al. | 23/254 R X |
| 3,837,808 | 9/1974 | Sugimoto et al. | 23/232 E |
| 3,882,028 | 5/1975 | Zolner | 23/254 E X |
| 3,915,645 | 10/1975 | Funke et al. | 23/232 R |
| 3,967,933 | 7/1976 | Etess et al. | 23/232 R X |
| 3,977,836 | 8/1976 | Matsuda et al. | 23/232 R |

*Primary Examiner*—Joseph Scovronek
*Attorney, Agent, or Firm*—Cushman, Darby & Cushman

[57] ABSTRACT

A method of testing a body of fluid for the presence of at least one component in which a measuring means is exposed successively to two masses of fluid derived from the body of fluid, the two masses differing in respect of the concentration of an active component to which the measuring means is sensitive by an amount dependent upon the concentration in the body of fluid of the at least one component to be detected, the measuring means being exposed to at least one of the two masses of fluid for a time sufficient for the measuring means to reach a known proportion less than one hundred percent of its equilibrium state with the active component in the fluid to which the measuring means is exposed. The two masses may be derived from the same sample or from different samples of the body of fluid.

14 Claims, 12 Drawing Figures

METHODS AND DEVICES FOR DETERMINING THE CONCENTRATION OF A COMPONENT OF A FLUID

This invention relates to methods and devices for determining the concentration of a component of a fluid.

In an instrument for monitoring the concentration of a component of a fluid over long periods of time, there is a risk of a slow monotonic change in the zero setting of the instrument, i.e., zero drift due, for example, to temperature changes. It is an object of this invention to minimise the effect on a reading of zero drift. Another problem may be that, depending on the fluid being measured, a measuring instrument may require a considerable period before equilibrium is reached and a steady reading is provided. Some embodiments of the invention are intended to minimise such problems.

In this specification the term 'active component' means a component to which a measuring means is sensitive.

According to the invention, a method of testing a body of fluid for the presence of at least one component comprises exposing a measuring means successively to two masses of fluid derived from said body of fluid, the two masses differing in respect of the concentration of an active component by an amount with is dependent upon the concentration in said body of fluid of the at least one component to be detected, and the measuring means being responsive to the concentration of said active component in the fluid to which the measuring means is exposed.

In one method the two masses of fluid are derived from a single sample of the body of fluid and a modifying step to bring about the difference in concentration is applied to the sample between said successive exposures of the measuring means. In another method each mass of fluid is derived from a different sample of the body of fluid, and a modifying step to bring about said difference in concentration is applied to one sample.

In one method the at least one component is an active component and the modifying step removes the active component.

In another method the modifying step converts the at least one component into an active component.

In another method the modifying step removes the at least one component, the concentration of the active component in the fluid being dependent on the concentration of the at least one component.

Also according to the invention, apparatus for testing a body of fluid for the presence of at least one component comprises a measuring means responsive to the concentration of an active component; and means for exposing the measuring means successively to two masses of fluid derived from said body of fluid, the two masses differing in respect of the concentration of the active component by an amount which is dependent upon the concentration in said body of fluid of the at least one component to be detected.

It will be understood that when a mass of fluid from which the active component is absent contacts the measuring means, a datum or zero level signal is produced, and when a mass of fluid which contains the active component contacts the measuring means, a signal related to the concentration of the active component is produced. By detecting the difference between the two alternately-provided signals, the concentration of the active component can be determined and any zero drift in the apparatus can be compensated. The zero signal and the concentration-related signal may either be provided both from the same sample, or the zero signal may be provided from a next preceding or next succeeding sample of the body of fluid. The apparatus may either be continuously operating, when groups of these two signals are provided with substantially no time delay between them, or may be intermittently operating when there will be a delay between each group of two signals.

Several embodiments of the invention will now be described by way of example with reference to the accompanying drawings in which.

Figure 1:
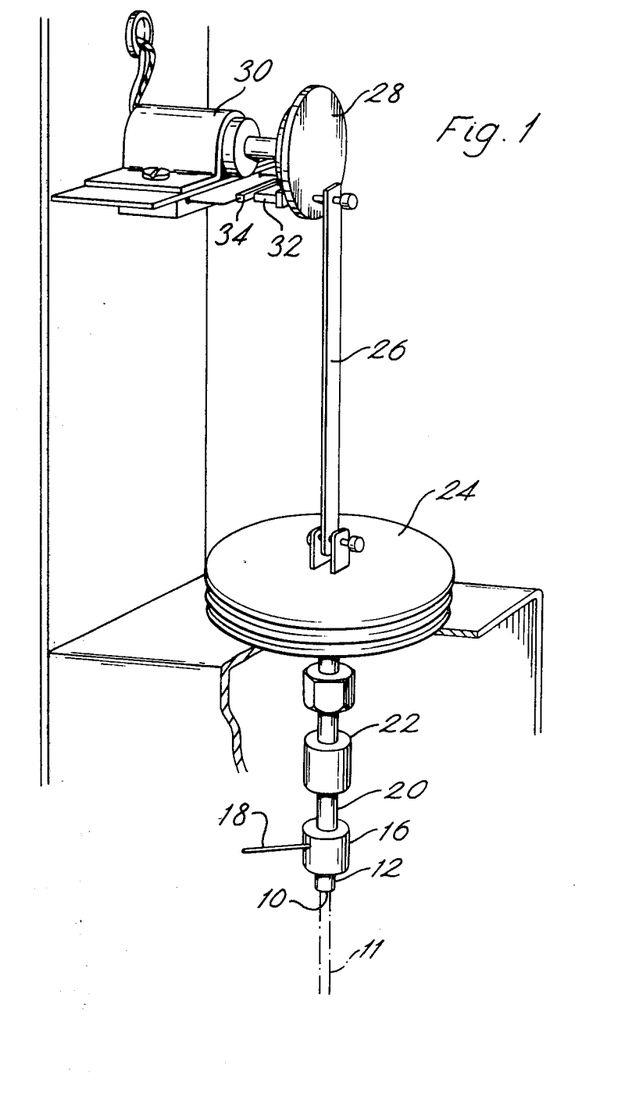
FIG. 1 is a view of the mechanical parts of a continuously operating carbon monoxide monitoring device.
Figure 3:
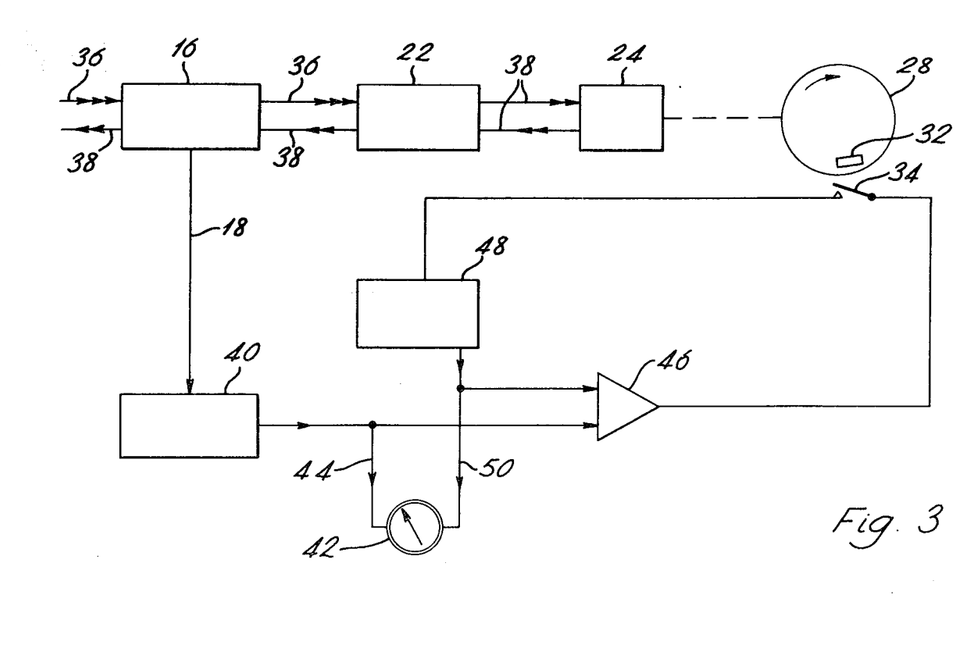
FIG. 3 is a schematic block diagram of the mechanical and electrical parts of the device shown in FIG. 1.

In FIG. 1, a sampling tube 12 is connected to a throughflow transducer 16, such as an electrochemical detector, which is sensitive to carbon monoxide (the active component in this embodiment) and which is electrically connected by a cable 18 to the electrical circuit shown in FIG. 3. Still referring to FIG. 1, the transducer is connected by a tube 20 through a carbon monoxide scrubber 22, suc as a palladium/alumina mixture which catalyses the oxidation of CO gas by atmospheric oxygen, to a valveless rubber bellows pump 24. The pump is operated by a crankshaft 26 connected eccentrically to a crank 28 which can be rotated by a low power electric motor 30. The crank 28 carries a magnet 32 near its periphery and the motor casing supports a normally open reed switch 34 which can be closed by proximity of the magnet.

In operation, the nozzle 10 of the tube 12 is placed in an atmosphere which may contain carbon monoxide. Rotation of the crank 28 causes reciprocation of the crankshaft and operation of the bellows pump 24. As the bellows expand, a sample of the atmosphere is drawn through the transducer 16 which provides a signal linearly related to the concentration of any carbon monoxide in this mass of fluid. The sample passes through the scrubber 22, which removes the carbon monoxide, into the bellows pump 24. As the bellows contract, the carbon-monoxide-free air is expelled through the scrubber 22, tube 20, transducer 16 and the tube 12, into the atmosphere, the transducer then providing a reading related to the carbon-monoxide-free mass of fluid. By subtracting the signal produced by passage of the mass of fluid in which carbon monoxide is absent from the signal produced by passage of the mass of fluid when carbon monoxide is present, the effect of any zero drift on the measured concentration of CO gas can be reduced or eliminated. The bellows pump operates continuously, and it is convenient to subtact the carbon-monoxide-free signal from a preceding sample of the body of fluid from the carbon-monoxide-present signal from a succeeding sample of the body of fluid. The maximum error which can occur is then limited to the zero drift which develops during one cycle of the apparatus. A typical cycle time is 2 minutes. Alternatively the signals from a single sample of the body of fluid before and after modification may be used.

Figure 2:
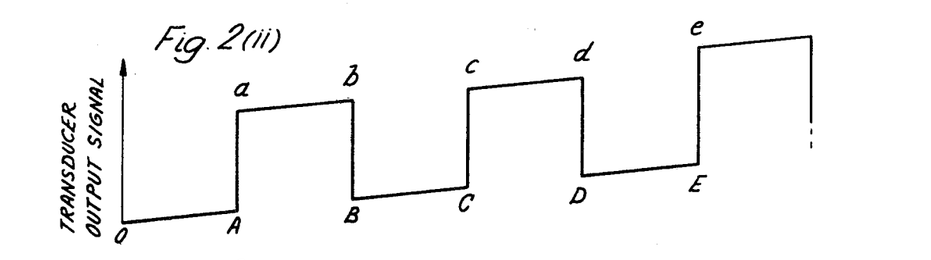
FIG. 2 indicates examples of the sequence of signals which may be provided by the device shown in FIG. 1.
Figure 2I:
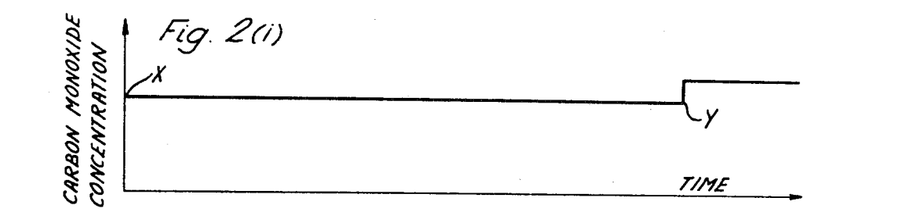

The mode of operation is illustrated in FIG. 2. Suppose carbon monoxide is present in an atmosphere at a constant concentration as shown in FIG. 2(i) by the line XY. If the transducer were not exposed to the atmosphere, the output signal would increase as indicated in FIG. 2(ii) by the line OABCDE due to zero drift, which is highly exaggerated for clarity. The drift is shown here as positive, but may also be negative. The bellows pump draws the atmosphere through the transducer during periods AB and CD and expels it during periods OA, BC and DE. When carbon monoxide gas passes into the transducer, the output signal increases rapidly from A to $a$, and then, due to zero drift, continues to increase along the line $ab$, while a mass of fluid containing CO gas at an unvarying concentration passes through the transducer, then falls to point B when scrubbed air is expelled by the bellows through the transducer. The true concentration is represented by the heights A$a$, B$b$, C$c$, D$d$, which are all equal because the concentration is constant. If the reading at point A is subtracted from the reading at point $a$, the concentration will be measured with no zero drift error. If the reading at point A is subtracted from the reading at point $b$, the error will be the difference between readings at A and B, which is small and is usually an acceptable error. If, in the next cycle, the reading at point C is subtracted from the reading at point $d$, the zero drift error will not be cumulative and will be less than the error developing during one cycle. If the CO concentration suddenly increases, (FIG. 2(i)), in the next cycle the height E$e$ will be greater than height D$d$.

A circuit for making the subtractions automatically is shown in FIG. 3. The transducer 16, scrubber 22 and pump 24 are shown schematically, the movement of air plus CO gas is shown by the triple arrows 36, and the movement of carbon-monoxide-free air is shown by the double arrows 38. At a certain point in the rotation of the crank 28, the magnet 32 closely approaches the reed switch 34 which then closes. As the disc rotates further, the reed switch opens again.

In the electrical part of the circuit the electrical signals are indicated by the single arrows. The transducer 16 is connected to an amplifier 40 which supplies a first side of a display meter 42 through a lead 44, and also supplies the first input of a comparator 46. The second comparator input is supplied from an analogue store 48 in a servo loop which includes the reed switch 34 and the comparator output. The analogue store is also connected to a second side of the meter 42 through a lead 50.

As a mass of fluid is expelled, the transducer 16 provides a signal related to the carbon-monoxide-free air; when most of the mass of fluid has been expelled, the magnet 32 closes the reed switch 34 and the comparator adjusts the level of the signal stored in the analogue store until it equals the amplified signal from the transducer, which represents point A in FIG. 2(ii).

As the next succeeding sample is drawn in, the transducer 16 provides a signal related to the concentration of carbon monoxide in the next sample, and the meter 42 displays the difference between this signal and the stored signal, that is, point A is subtracted from the signal equivalent to the line $ab$ in FIG. 2(ii). The zero drift in this signal will usually be so small that it is not detectable during a single reading, but a cumulative error over several cycles would affect the reading. In the next cycle the analogue store is reset so that point C will be subtracted from the line $cd$; thus the zero error is not cumulative.

The analogue store may be a capacitor with a voltage follower system having a time constant which is long compared with the pump cycle to prevent the meter reading being affected by capacitor leakage.

The mode of operation shown in FIG. 2(ii) assumes that the transducer responds to the presence of carbon monoxide instantaneously. If however the transducer has a slow response to the presence of CO gas, the output signal would be as shown in FIG. 2(ii) in which the true readings in the presence of CO gas are approached asymptotically; the signal level in the absence of CO gas is also approached slowly. In such circumstances, the bellows pump must be operated sufficiently slowly to allow equilibrium to be reached when CO gas is present or absent. Conveniently, the apparatus shown in FIG. 1 may be modified to provide a completely manually-operated device. Suppose the crankshaft 26 is disconnected from the bellows 24 and replaced by a handle, and suppose there are provided locking devices to hold the bellows in both the fully expanded and fully contracted positions until manually released. Then the bellows could be manually expanded until one locking device operates, left until an equilibrium signal is reached, manually contracted until the other locking device operates, and left until an equilibrium signal is reached. Alternatively the device could be operated by a reversing motor; the time intervals between the pump strokes could then be selected as required. In either arrangement, in order to prevent the diffusion of the atmosphere into the detector when the bellows is locked in position, a long narrow tube, shown dotted at reference 11 in FIG. 1, should be provided in addition.

Referring again to automatic apparatus, if the length of time required for a cycle is excessive, for example if a frequent alarm signal is required, the apparatus may be operated in the mode shown in FIG. 2(iv) which will be referred to as the limited contact time mode. The cycle time of the pump is considerably shorter than previously, the time taken for the bellows to expand is accurately controlled and is chosen so that the transducer signal in the presence of CO gas does not reach equilibrium, but in each cycle reaches a known proportion of the equilibrium signal. The bellows then contracts and the transducer provides a signal which reaches the correct absence-of-CO gas level, including zero draft. Such an arrangement allows many readings of the concentration of a gas to be provided in a short time, which may be advantageous if the zero error increases rapidly, and which allows a single reading to be provided very rapidly for alarm purposes.

It may alternatively or additionally be the approach to a correct signal level in the absence of CO gas which is not allowed to reach an equilibrium level, but preferably one signal is allowed to reach equilibrium.

The times taken to expand and to contract the bellows will now need to be controlled so as to be unequal. For example in FIG. 2(iv) bellows expansion time $t_1$ is shorter than bellows contraction time $t_2$. The apparatus shown in FIG. 1 must then be modified by replacing the crank 28 by a cam of the appropriate shape. For an electrochemical carbon-monoxide detector, typically $t_1$ is 12 seconds and $t_2$ is 48 seconds.

Figure 4:
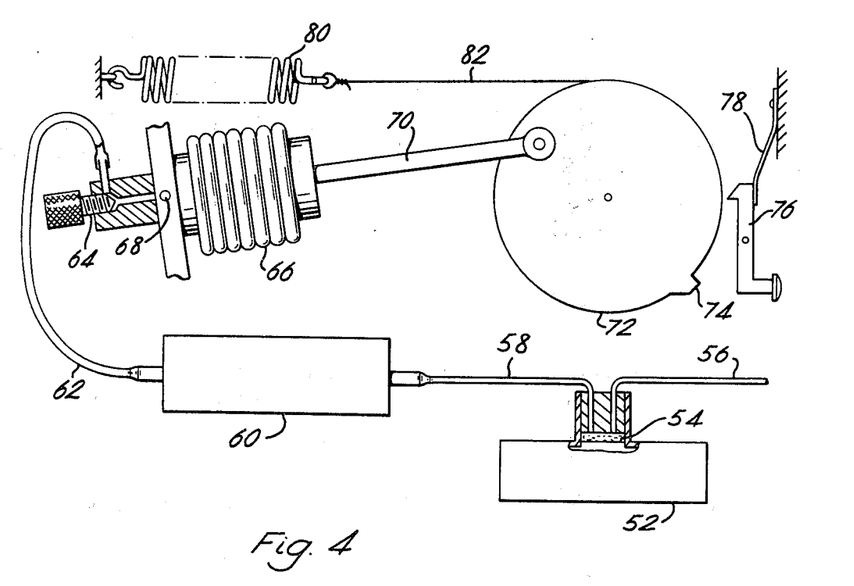
FIG. 4 is a view of the mechanical parts of one type of manually triggered carbon monoxide measuring apparatus.

FIGS. 1 and 3 illustrate components of an automatically and continuously operating gas monitor. The invention may also be applied to a device which provides a single reading of the concentration of an active component when manually triggered, but is intended to be able to be triggered a large number of times in succession, to provide an interrupted sequence of operation. Such a device is shown in FIG. 4 in which a carbon monoxide sensor 52 is connected through a sintered disc 54 and a sampling tube 56 to the atmosphere, and through the disc 54 and a second tube 58 to a carbon-monoxide scrubber 60. The scrubber is connected by a flexible tube 62 through an adjustable flow-restricting valve 64 to a bellow pump 66 which is pivoted at 68 and is operated by a crankshaft 70. The crankshaft is connected to a crank 72 having a projection 74 which co-operates with a manually-operable trigger 76 loaded by a leaf spring 78. The crank is also arranged to act as a pulley by attachment to a spring 80 by a pulley cord 82.

Considering now the operation of the bellows pump; to cock the device the crank is manually rotated clockwise from the position in which it is shown until the projection 74 is latched by the trigger 76; this causes the spring 80 to be expanded by the pulley cord 82 which is wound around the crank, and the bellows pump is expanded then fully contracted. When the trigger 76 is released, the crank is rotated anticlockwise through about 270° by the contraction of the spring 80. The bellows are first fully expanded, then partly contracted. The crank 72 is then manually rotated and the trigger 76 cocked once more.

As the bellows are expanded when the trigger is cocked, atmospheric gas is drawn through tube 56, past the sensor 52, through tube 58 and the scrubber 60 into the bellows. The bellows therefore contain carbon-monoxide-free air. The succeeding complete contraction of the bellows during cocking expels this air past the sensor 52 which provides a zero or datum signal. When the trigger is released, the resulting full expansion of the bellows draws a carbon-monoxide-containing sample of atmospheric past the sensor, which provides a signal related to the concentration of CO gas. The succeeding partial contraction of the bellows once again expels CO-free air past the sensor 52 and provides a clearly defined limited contact time mode of operation. As with the device illustrated in FIG. 1, the zero or datum signal from a preceding sample can be used to correct zero error in the measurement of a next succeeding sample. The delay between successive operations of the trigger must not be so long that carbon monoxide diffuses into the sensor from the surrounding atmosphere. At the beginning of a sequence of tests the first few readings may be incorrect for this reason.

The flow-restricting valve 64 may be varied to control the time taken for the bellows to expand when triggered. The sampling tube 56 should be sufficiently long to prevent diffusion of the atmosphere to the sensor during the periods when the device is cocked. Alternatively the tube may be sealed during such periods.

It is a particular advantage of this arrangement that a portable gas detector can be provided. The device may also be modified by replacing the crank and crankshaft by a second helical spring and a second trigger so that operation of the first trigger allows the first helical spring to expand the bellows, then operates the second trigger which allows the second helical spring to partially contract the bellows. Both triggers would be manually set when the device was cocked. The device may be operated in a limited contact time mode whichever driving arrangement is provided.

The output of the sensor 52 shown in FIG. 4 when manually operated would be similar to that shown in FIG. 2(iv), but with intermittent peaks.

Figure 5:
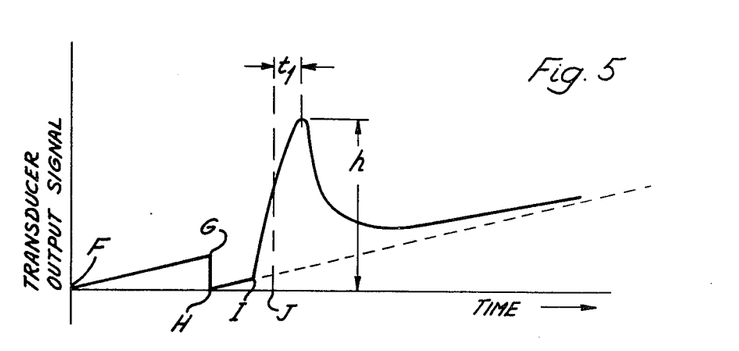
FIG. 5 indicates the sequence of signals provided by the device shown in FIG. 4.

FIG. 5 shows a likely sequence of responses, once again with an exaggerated zero drift. Conveniently a display meter or chart recorder to which the output of the sensor is connected is set to zero, e.g. at point F, once the transducer has been flushed out with carbon-monoxide-free air by fully cocking the device shown in FIG. 4. Zero drift will cause the reading to vary slowly along the line FG. When a measurement of CO gas concentration is required, the meter is set manually to zero, point H. As soon as possible, say at point I, the trigger is released, and a CO containing mass of fluid is supplied to the sensor for a fixed time interval IJ. The sensor output rises to a peak of height $h$, representing the CO concentration. The time delay $t$, between the time at which the CO supply is terminated, J, and the maximum sensor output, is due to the finite response time of the transducer.

At the time represented by point J, CO-free air is supplied to the sensor by the return movement of the bellows, and the output of the sensor returns to the zero drift baseline. The procedure may then be repeated as from point F by cocking the device. The height of the peak is minimally affected by zero drift. It represents also a relatively quickly obtained measure of the CO concentration.

The apparatus shown in FIGS. 1, 3 and 4 has been described with reference to the detection of carbon monoxide gas either by a fast response measuring means or by a slow response measuring means operated in a limited contact time mode. Many other gases may also be detected by choice of suitable measuring means and scrubber, but it is not always possible to provide a fast-response measuring means. Further, some gases such as sulpher dioxide are prone to adsorb on the surfaces of the apparatus with which the gas comes into contact, and incorrect measurements may be obtained if such adsorption is not complete. As an alternative to the limited contact time mode, it may be convenient to keep a device continually equilibrated with an atmosphere containing an active component which is to be measured, except when a modified sample is being caused to flow past the measuring means.

Figure 6:
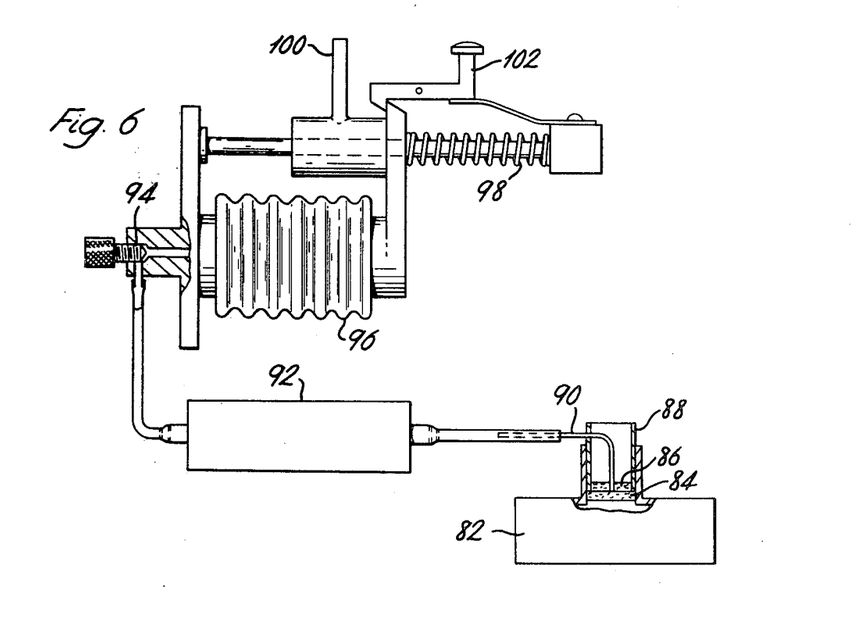
FIG. 6 is a view of the mechanical parts of another type of manually triggered device which can be continually equilibrated with a test atmosphere.

Such a device is shown in FIG. 6 in which a sulphur dioxide sensor 82 is connected through two sintered bronze discs 84, 86 and a diffusion chimney 88 directly to an $SO_2$ gas-containing atmosphere. The sensor is also connected through disc 84 to a tube 90 connected to a $SO_2$ scrubber 92 which in turn is connected through a flow-restricting valve 94 to a bellows pump 96 operated by a compression spring 98. The spring 98 can be manually compressed by a loading handle 100 and held in the cocked position by a spring-loaded trigger 102.

In operation, the trigger of the device is cocked, the atmosphere diffuses to the sensor 82 through the sintered discs 84, 86 and the $SO_2$ concentration at the sensor is maintained, so that the sensor can slowly approach equilibrium. This provides a datum, (no longer a true zero) signal. When the trigger is operated, the spring 98 compresses the bellows and expels $SO_2$-free scrubbed gas past the sensor 82. This provides a limited contact time mode of operation. The dip in the signal is proportional to the concentration of $SO_2$ gas in the atmosphere. Once the bellows has reached the end of its movement, $SO_2$ gas will diffuse to the sensor again from the atmosphere and the datum signal will again be approached. The datum signal will thus alter both because of zero drift and also because of changes in the concentration of $SO_2$ gas in the atmosphere. However, no return movement of the bellows is required for a measurement to be made. Alternatively, the $SO_2$-free gas may be provided from a separate source such as a gas bottle which has initially been filled by causing atmospheric gas to pass through a layer to remove all $SO_2$ gas it may contain.

In this mode, unlike the mode in which there is a diffusion-rate-limiting tube between the sensor and the atmosphere, such as tube 11 in modified FIG. 1 and tube 56 in FIG. 4, the sensor will respond to changes in the atmospheric concentration of the gas being detected, even without operation of the bellows. This enables fluctuations in concentration to be more easily detected.

Figure 7:
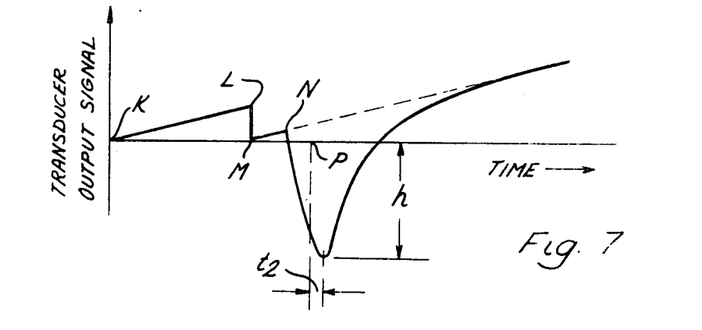
FIG. 7 indicates the sequence of signals provided by the device shown in FIG. 6.

The sequence of operation is illustrated in FIG. 7. Conveniently, a display meter or chart recorder, to which the output of the sensor is connected, is set to zero, e.g. at point K, when equilibrated with $SO_2$ gas in air. Zero drift will cause the output to vary slowly along the line KL. When a measurement of $SO_2$ gas concentration is required, the meter is set manually to zero point M, and as soon as possible, say point N, the trigger is released, $SO_2$-free air is supplied to the sensor, and the output signal decreases, the bellows reaches the end of its movement at point P, and gas will diffuse to the sensor again from the atmosphere. This provides a limited contact time mode of operation. The siganl shows an inverted peak of height $h$ proportional to the concentration of $SO_2$ gas in the atmosphere and minimally affected by zero drift. The signal then approaches the zero drift baseline again, unless the $SO_2$ concentration has altered in the interim. The procedure may then be repeated as from point K by cocking the device. The time delay $t_2$ between termination of the supply of $SO_2$-free air and the minimum reading is due to the finite response time of the transducer.

If the $SO_2$ concentration suddenly increased, the display meter readng would also suddenly increase. To measure the new concentration, the meter is set manually to zero, the trigger released immediately and the new, higher, $SO_2$ gas concentration is represented by a greater height of the inverted peak (not shown).

With both the devices shown in FIGS. 4 and 6, electrical circuits may be provided so that after initially operating a switch, a corrected reading is obtained automatically, as described with reference to FIGS. 1 and 3.

In the invention as described so far, a mass of fluid free of a particular component has been obtained by passage through a scrubbing layer in one direction, and then back through it in the other direction. However, it may, in some instances, be important to have a constant flow through the absorber or other modifying means, for instance to preserve a certain degree of selectivity of treatment of a pair of pollutants. This could be achieved by pumping the atmosphere in two streams in parallel; one through a scrubber layer, the other through an inactive layer of equivalent flow resistance.

Valves would then be switched cyclically to direct each gas stream in turn to the sensor, and to a vent. If an active-species-containing atmosphere were directed to the sensor for about 12 seconds and the scrubbed stream for 48 seconds in each minute, the sensor would show a response like that in FIG. 2(IV).

Figure 8:
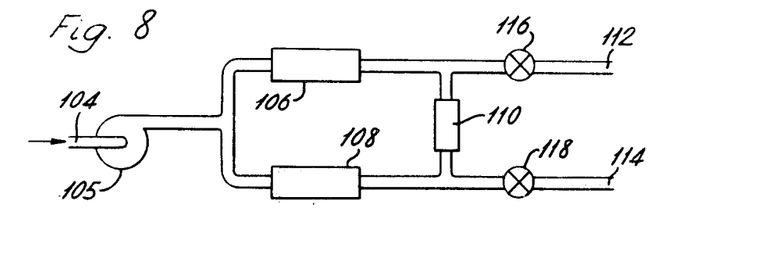
FIGS. 8 and 9 show alternative gas flow systems.

An arrangement to achieve this effect is shown in FIG. 8. Gas from an atmosphere under test is drawn through an inlet tube 104 by a pump 105 and passes either through a scrubbing layer 106 or through an inactive layer 108 which has a flow resistance equivalent to that of the scrubbing layer. The outlets of the layers 106 and 108 are connected to opposite ends of a throughflow transcducer 110 and to respective outlet tubes 112, 114, closed by respective valves 116, 118 which are arranged to operate so that one is open and the other closed, in alternation. The transducer 110 is assumed to have negligible flow resistance, so the flow through the scrubbing layer 106 should be the same whichever valve is open. In one arrangement, the connecting tubes between the items of apparatus are relatively elastic silicone rubber tubing, and the valves comprise means to clamp the outlet tubes.

Figure 9:
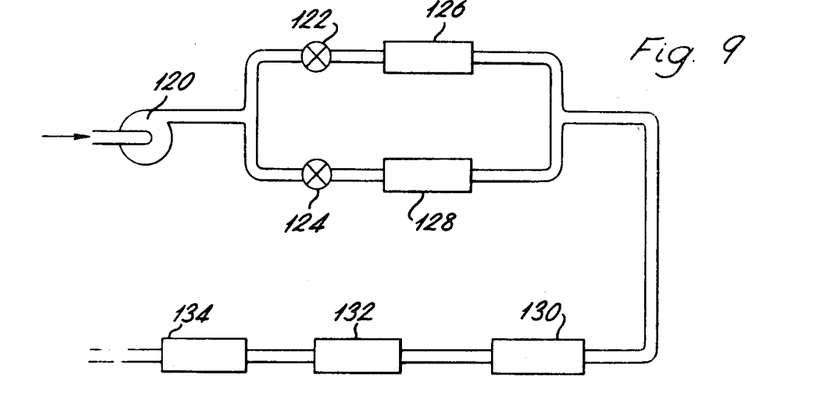

An alternative arrangement is shown in FIG. 9, in which a pump 120 pumps gas through two alternately acting valves 122, 124, either to a scrubbing layer 126 (which is the modifying means of the invention) or to an inactive layer 128. After passage through one of the layers, the gas passes through a chromatographic column 130, a furhter modifying means 132 and a sensing means 134. In this arrangement, the chromatographic column separates different gas species in time so that they can be detected individually by the sensing means 134. The modifying means 132 is necessary only if the gas to be detected is not an active component. For example, if vinyl chloride monomer is to be detected, the modifying means may be a permanganate layer to convert the vinylchloride to chlorine, and the sensing means 134 can be sensitive to chlorine.

In the embodiments of the invention described above, the active component has always been present in an atmosphere from which the sample is taken, and is then removed from the sample by scrubbing means. In the devices illustrated in FIGS. 1 and 4, expansion of the bellows has provided a measuring signal and contraction of the bellows a zero or datum signal. If, however, the component which is to be detected is a gas for which no accurate or cheap or otherwise desirable measuring means exists, i.e., is not an 'active component' within the definition at the beginning of this specification, then the component may be modified, for example by chemical reaction, to form another component which is an 'active component'. In such circumstances the scrubbing means is replaced by, for example, a catalyst layer. The active component is then present in the bellows pump after passage through the modifying means, the expansion of the bellows provides the zero or datum signal, and contraction provides the measuring signal.

For example suppose the concentration of nitric oxide gas NO is to be measured. A measuring means sensitive to nitrogen dioxide gas but insensitive to NO gas is provided and the scrubber in, for example, the device shown in FIG. 1 or FIG. 4, is replaced by a chromic acid catalyst layer. A sample of the atmosphere is drawn past the measuring means and a zero or datum signal is provided. The sample passes over the chromic acid and any NO gas is oxidised by atmospheric oxygen to a proportionate concentration of $NO_2$ gas. The modified sample is the expelled, and the concentration of $NO_2$ gas is measured.

The arrangement may also be used to measure the concentration of NO gas even in the presence of $NO_2$ gas, because the datum signal when the bellows expand will be related to the concentration of $NO_2$ and the measuring signal when the bellows contract will give a measure of NO converted to $NO_2$ plus original $NO_2$; the difference is proportional to the concentration of NO gas.

In another modification, if the sum of the concentrations of an active component and an inactive component of an atmosphere are required, the inactive component may be converted to the active component before supply to the detector. For example, the sum of the concentrations of NO gas and $NO_2$ gas may be measured by drawing a sample of an atmosphere over a chromic acid layer to convert NO to $NO_2$, past a $NO_2$ sensor to give a concentration-dependent signal, through a $NO_2$ scrubbing layer, and again past the measuring means to provide a datum or zero signal.

In another modification, if an atmosphere contains two active components and the concentration of only one component is required, the addition of a selective scrubbing layer between the atmosphere and the detector may be required. For example, if the concentration of CO gas is to be measured in the presence of $NO_2$ gas, and the detector is sensitive to both gases, the addition of a charcoal layer between the detector and the atmosphere allows the removal of $NO_2$ gas before the sample reaches the sensor.

In another modification, the concentration of one gas in a gas mixture may be measured by measuring the concentration of another gas in the mixture, modifying the gas to be measured so as to change the partial pressure of said another gas, and again measuring the concentration of said another gas in the modified sample.

In one arrangement, a sample is caused to pass over an absorption layer which completely removes the gas to be measured. For example to measure concentration of carbon dioxide gas in the atmosphere it is possible to measure the oxygen concentration in a sample of the atmosphere, pass the same or a different sample through a $CO_2$ absorbent, and measure the oxygen concentration in the modified sample. The difference in the measured partial pressures of oxygen can be used to calculate the $CO_2$ concentration.

In another arrangement a sample is caused to pass over catalytic or reactive means to convert the gas to be measured into another gas to which the measuring means is not sensitive; to alter the partial pressure in this case it is essential that each molecule of the gas to be measured is converted to a higher or lower number of molecules of said another gas.

In yet another arrangement, the gas to be measured is caused to react with the active component itself, which must be present in excess.

While the invention has been described with reference to the measurement of the gases CO, $CO_2$, NO, $NO_2$, $SO_2$ and vinyl chloride in air, it is not limited to such gases but can be used to determine the concentrations of other gases in air, of a component of a gas mixture, and of a component of a liquid mixture or solution.

It has been assumed throughout this specification that the measuring means, i.e., the transducers or sensors, are not flow-rate dependent.

I claim:

1. A method of testing a body of fluid for the presence of at least one component comprising exposing a measuring means successively to two masses of fluid derived from said body of fluid, one mass having been subjected to a modifying step whereby the two masses differ in respect of the concentration of an active component by an amount which is dependent upon its concentration in said body of fluid of the at least one component to be detected, the measuring means being responsive to the concentration of said active component in the fluid to which the measuring means is exposed, the measuring means being exposed to at least one of the two masses of fluid for a time sufficient for the measuring means to reach a known proportion less than one hundred percent of its equilibrium state with any active component in the fluid to which the measuring means is exposed.

2. A method according to claim 1 in which the two masses of fluid are derived from a single sample of the body of fluid, the modifying step being applied to the sample between said successive exposures of the measuring means.

3. A method according to claim 1 in which each mass of fluid is derived from a different sample of the body of fluid.

4. A method according to claim 1 in which the at least one component is an active component, and the modifying step removes the active component.

5. A method according to claim 1 in which the modifying step converts the at least one component into an active component.

6. A method according to claim 1 in which the modifying step removes the at least one component, the concentration of the active component in the fluid being dependent on the concentration of the at least one component.

7. Apparatus for testing a body of fluid for the presence of at least one component comprising a measuring means responsive to the concentration of an active component; means for exposing the measuring means successively to two masses of fluid derived from said body of fluid; and modifying means for modifying one mass whereby the two masses differ in respect to the concentration of the active component by an amount which is dependent upon the concentration in said body of fluid of the at least one component to be detected, the measuring means being exposed to at least one of the two masses of fluid for a time sufficient for the measuring means to reach a known proportion less than one hundred percent of its equilibrium state with any active component in the fluid to which the measuring means is exposed.

8. Apparatus according to claim 7 comprising means to cause a sample of the body of fluid to flow past the measuring means, past the modifying means, and again past the measuring means, the sample before and after modification comprising said two masses of fluid.

9. Apparatus according to claim 7 comprising means to cause a succession of samples of the body of fluid to flow past the measuring means, past the modifying means, and again past the measuring means, a preceding sample after modification and a succeeding sample before modification comprising said two masses of fluid.

10. Apparatus according to claim 7 comprising means for exposing the measuring means substantially continuously to the body of fluid, and intermittently operating means for causing a modified sample of the body of fluid to flow past the measuring means, the part of the body of fluid in contact with the measuring means and the modified sample comprising said two masses of fluid.

11. Apparatus according to claim 7 comprising means to cause alternate samples of the body of fluid to flow respectively past the measuring means, and past the modifying means then past the measuring means.

12. Apparatus according to claim 11 comprising means to cause alternate samples of the body of fluid to flow respectively past the modifying means and past inactive means of similar flow resistance whereby a constant flow rate is maintained through the modifying means.

13. Apparatus according to claim 7 further comprising a chromatographic column arranged between the body of fluid and the measuring means whereby a plurality of components to be detected can be separated in time.

14. Apparatus according to claim 7 in which the measuring means is arranged to provide an output signal related to the concentration of the active component in each of the two fluid samples, there being further provided subtraction means arranged to subtract one signal from the other and to provide a third output signal related to the concentration of the active component in one of the two masses of fluid.

* * * * *